United States Patent [19]

Salmond

[11] 4,066,665
[45] Jan. 3, 1978

[54] 2-ALKYLAMINO-α-PHENYL-1-CYCLOHEXENE-1-METHYLENEIMINE, ITS SALTS AND PREPARATION

[75] Inventor: William G. Salmond, Mount Arlington, N.J.

[73] Assignee: Sandoz, Inc., E. Hanover, N.J.

[21] Appl. No.: 480,626

[22] Filed: June 19, 1974

Related U.S. Application Data

[62] Division of Ser. No. 160,960, July 8, 1971, abandoned.

[51] Int. Cl.² ............................................. C07D 333/12
[52] U.S. Cl. ........................ 260/332.5; 260/329 AM; 260/566 R; 424/275; 424/325
[58] Field of Search ......... 260/566 R, 329 AM, 332.5

[56] References Cited

U.S. PATENT DOCUMENTS

| | | | |
|---|---|---|---|
| 3,553,199 | 1/1971 | Atcher et al. | 260/566 |
| 3,723,432 | 3/1973 | Ott | 260/566 |

*Primary Examiner*—Bernard Helfin
*Assistant Examiner*—Alan Siegel
*Attorney, Agent, or Firm*—Gerald D. Sharkin; Richard E. Vila

[57] ABSTRACT

Compounds of the formula

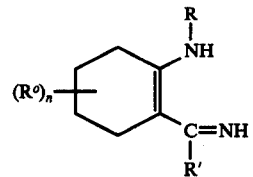

wherein R and R° are lower alkyl, R' is optionally substituted phenyl or 2-thienyl and $n$ is 0 to 2, and their salt forms, are prepared by reacting a compound of the formula:

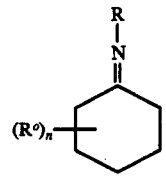

with an aromatic nitrile and strong base, and quenching with water when the free base form is desired, said first mentioned compounds being intermediates for quinazolinones.

10 Claims, No Drawings

2-ALKYLAMINO-α-PHENYL-1-CYCLOHEXENE-1-METHYLENEIMINE, ITS SALTS AND PREPARATION

This is a division of application Ser. No. 160,960 filed July 8, 1971, now abandoned.

This invention relates to the preparation of 1-substituted4-cyclosubstituted tetrahydro quinazolinones and intermediates and to certain novel compounds thereby.

The compounds of this invention include compounds of the formula I:

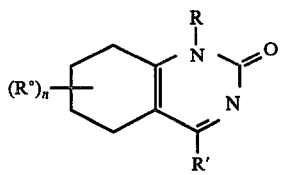

wherein:
- R° is lower alkyl, preferably containing 1 to 3 carbon atoms,
- n is 0, 1 or 2,
- R is lower alkyl, preferably containing 1 to 5 carbon atoms, e.g., methyl, ethyl, propyl, isopropyl, butyl, isobutyl and sec butyl,
- R' is a radical of the formula

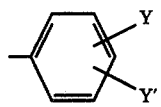

in which Y and Y' are the same or different and represent hydrogen, halo of atomic weight of 19 to 36, lower alkyl, preferably containing from 1 to 2 carbon atoms, e.g., methyl or ethyl, lower alkoxy, preferably containing from 1 to 2 carbon atoms, e.g., methoxy or ethoxy, or one of Y and Y' is trifluoromethyl while the other is hydrogen, or a radical of the formula

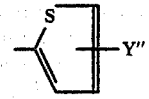

in which Y" is hydrogen, fluorine, chlorine or alkyl of 1 to 3 carbon atoms.

This invention also comprises:
a. preparing a compound of the formula I, above, by cyclizing a compound of formula II

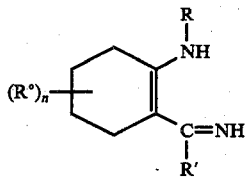

in which R, R', R° and n are as defined above, with phosgene, and
b. preparing a compound of the formula Ia

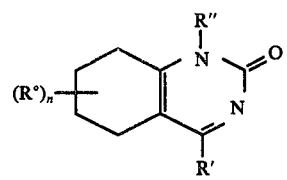

in which R', R° and n are as defined above, and R" has the same significance as R, defined above, except that it may not signify a tertiary alkyl group in which the tertiary carbon atom is directly attached to the ring nitrogen atom, by cyclizing a compound of formula IIa

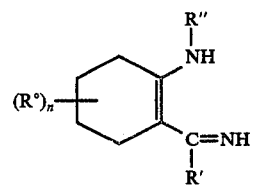

wherein R°, R', R" and n are as defined above with a carbonic acid derivative selected from the group of
i. a $C_{1-2}$ alkyl chlorocarbonate and
ii. a 1,1'-carbonyldiimidazole.

Process (a) is suitably carried out at a temperature of from −30° C. to +50° C., preferably −5° C. to 30° C. The reaction may be carried out in an organic solvent which is inert under the reaction conditions, suitably an aromatic hydrocarbon, e.g., benzene, toluene or xylene, preferably toluene. Other suitable solvents include dioxane. The mole ratio of the phosgene to the compound of formula II is not particularly critical, but a substantial excess of the phosgene is preferably employed. The process may optionally be carried out in the presence of an acid-binding agent such as an inorganic base, e.g. a trialkylamine or pyridine, preferably triethylamine. The reaction time may range for ½ to 10 hours, more usually 1 to 4 hours.

Process (b) (i) is suitably carried out at a temperature of from −30° C. to 100° C., preferably −0° C. to +30° C. The reaction may be carried out in an organic solvent which is inert under the reaction conditions, suitably an aromatic hydrocarbon, e.g., benzene, toluene or xylene, preferably toluene. Other suitable solvents include dioxane or the alkyl chlorocarbonate. The mole ratio of the chlorocarbonate to the compound of formula IIa is not particularly critical, but a substantial excess of the alkyl chlorocarbonate is preferably employed. The process may optionally be carried out in the presence of an acid-binding agent such as an inorganic base, e.g., a trialkylamine or pyridine, preferably triethylamine. The reaction time may range for ½ to 10 hours, more usually 1 to 4 hours.

Process (b) (ii) is suitably carried out at a temperature of from 0° C. to 120° C., preferably 40° C. to 90° C. The reaction is preferably carried out in an organic solvent which is inert under the reaction conditions, suitably an aromatic hydrocarbon, e.g., benzene, toluene or xylene, especially benzene. An excess of 1,1'-carbonyldiimidazole is preferably employed.

The compounds of the formula I and Ia can be isolated from the reaction mixtures by working up by conventional procedures.

The compounds of formula II above can be prepared by reacting a compound of formula III

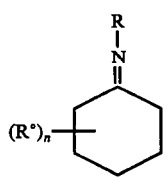    III in which R, R° and n are as defined above with a suitable strong base and a compound of formula IV

R'—C≡N    IV in which R' is as defined above, in an inert solvent to form a solution of the Salt A

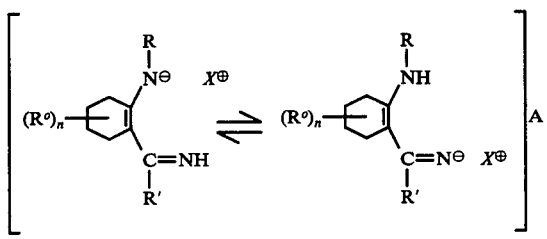    A in which R, R°, R' and n are as defined above, and X is a metal, preferably lithium or magnesium, and quenching the solution with water.

Suitable strong bases are those which are capable of removing a hydrogen atom from the methylene group in the cyclohexene ring adjacent to the amine function of compound III to provide the desired anion for reaction with the compound of formula IV. They include the alkali metal salts, especially the lithium salt, of secondary amines such as diethylamine, dimethylamine and diisopropylamine, as well as other bases such as methyl magnesium iodide. Lithium diisopropylamide, because of its relatively large size, is quite advantageous where there is an R° group in the meta position of the compound of formula III. One mol of the strong base and up to about 1.2 mols can be used per mol of the compound of formula III, preferably equimolar amounts are used.

The temperature of the reaction mixture is maintained at about 20° to 80° C.

Generally, the compound of formula III in a suitable solvent such as benzene, is added to a solution of the base in a suitable solvent and allowed to react for about 10 to 60 minutes. The compound of formula IV, neat or in a suitable inert solvent, is then added to the reaction mixture of the base and compound III. The compounds III and IV and the strong base may, however, be brought together simultaneously.

The resulting reaction mixture containing the salt of formula A can, at this point, be treated by process (a) or (b) above to yield directly the compound of formula I. Suitable temperature control should be exercised, as this reaction is more exothermic than when compound II is employed. However, the salt solution is advantageously quenched with water to obtain the compound of formula II, which can be reacted in situ according to process a) or b) to form compound I, but is preferably extracted and washed first using conventional methods.

The compounds of formula III can be prepared by reacting a compound of formula V

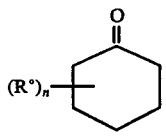    V wherein R° and n are as defined above, with a compound of formula VI

R—NH₂    VI wherein R is as defined above,
to eliminate one molecule of water, conveniently in the presence of a molecular sieve or a dehydrating agent, such as alumina, calcium chloride, phosphorus pentoxide or mixtures thereof.

This reaction can be carried out at temperatures from 0° to about 80° C., conveniently 20° to 30° C. In cases where the compound of formula VI is volatile, an excess is generally mixed with the compound of formula V and the unreacted portion removed by vacuum distillation after removal of the dehydrating agent. When the compound of formula VI is nonvolatile, equimolar proportions of compounds of formulae V and VI are mixed in suitable solvent such as benzene, the solvent then being removed in vacuo after completion of the reaction and after filtration of the dehydrating agent.

The compounds of formula V are known or can be produced in a known manner.

The compounds of formula I are useful because they possess pharmaceutical activity in animals. In particular, the compounds I are useful as anti-inflammatory agents as indicated by the Carrageenan-induced edema test in rats. For the above-mentioned use, the dosage administered will, of course, vary depending upon known factors such as the particular compound and mode of administration. However, in general, satisfactory results are obtained when administered at a daily dosage of from about 5 milligrams to about 200 milligrams per kilogram of body weight, preferably given in divided doses 2 to 4 times a day, or in sustained release form. For most mammals the administration of from about 300 milligrams to about 2000 milligrams of the compound per day provides satisfactory results and dosage forms suitable for internal administration comprise from about 75 milligrams to about 1000 milligrams of the compound in admixture with a solid or liquid pharmaceutical carrier or diluent.

The compounds of the formula I are also useful as analgesics as indicated by application of pressure to yeast-inflammed foot of the rat (oral administration). For such use, the compound may be administered to obtain satisfactory results in modes and forms similar to those employed in the treatment of inflammation and at dosages indicated above as applicable for the use of the compound in the treatment of inflammation.

For the above usage, oral administration with pharmaceutically acceptable carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents, and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g. magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g. suspending agents (methylcellulose, tragacanth and sodium alginate), wetting agents (lecithin, polyoxyethylene stearate and polyoxyethylene sorbitan monooleate) and preservatives (ethyl-p-hydroxy-benzoate). Capsules may contain the active ingredient alone or admixed with an inert solid diluent, e.g. calcium carbonate, calcium phosphate and kaolin. The preferred pharmaceutical compositions from the standpoint of preparation and ease of administration are solid compositions, particularly hard-filled capsules and tablets.

A representative formulation is a capsule prepared by conventional techniques and containing the following ingredients:

| Ingredient | Parts by Weight |
|---|---|
| Compound of formula I, e.g. 7-methyl-1-isopropyl-4-phenyl-5,6,7,8-tetrahydro-2(1H)-quinazolinone | 50 |
| Inert solid diluent e.g. kaolin | 200 |

Preferred compounds of formula I, from the point of view of pharmacological activity, are those in which R signifies an isopropyl radical.

The compounds of formula I are also useful as intermediates in the preparation of compounds of the formula VII

VII wherein R, R°, R' and n are as defined above.

The preparation of compounds VII from compounds I is effected by dehydrogenating the latter. This reaction can be carried out in the presence of a dehydrogenating agent, such as sulfur, selenium, a benzoquinone such as 2,3,5,6-tetrachloro-1,4-benzoquinone and 2,3-dichloro-5,6-dicyano-1,4-benzoquinone, tetracyanoethylene or triphenylmethyl perchlorate or a dehydrogenation catalyst, such as palladium on charcoal or nickel.

Where a dehydrogenating agent such as sulfur or a benzoquinone is used, at least 2 mols per mol of the compound I are employed, with the preferred amount being about 2 to 2.5 mols. Where a dehydrogenation catalyst is used, a catalytic amount sufficient to cause removal of two molecules of hydrogen per mole of compound of formula I is employed. Temperatures in the range of about 60° to 180° C., are employed. The particular temperatures, as well as the reaction time will depend upon the particular dehydrogenating agent or catalyst and the ease with which the starting material surrenders hydrogen, this in turn depending somewhat on the nature and location of R° and the value of n. A solvent is also used, such as xylene or other organic liquid having a sufficiently high boiling point. When a dehydrogenation catalyst is used, a hydrogen scavenger, such as nitrobenzene, is employed in place of or in addition to other solvents. The product can be isolated from the reaction mixture by working up by conventional methods.

When a dehydrogenation catalyst is used without a hydrogen scavenger, compounds of the formula VIII

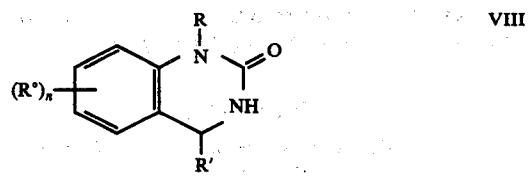

VIII wherein R, R°, R' and n are as defined above, are obtained.

Compounds VII and VIII are known and are useful as anti-inflammatory and analgesic agents.

The following examples illustrate the invention. Percentages are by weight and temperatures are in degrees Centigrade. Unless otherwise specified, the reactants are brought together under substantially ambient temperature and pressure conditions and no control of the reaction temperature is exercised.

EXAMPLE 1

1-Isopropyl-4-Phenyl-5,6,7,8-Tetrahydro-2(1H)-Quinazolinone.

Step A: 1-Methyl-N-(cyclohexylidene)-ethylamine

To a mixture of 600 g. cyclohexanone and 1 l. isopropylamine are added 500 g. Linde Type 3A molecular sieves. The mixture is allowed to stand overnight at room temperature, after which the isopropylamine is removed in vacuo at room temperature. The oily residue is 1-methyl-N-(cyclohexylidene)-ethylamine.

Step B:
1-Isopropyl-4-phenyl-5,6,7,8-tetrahydro-2(1H)-quinazolinone n-Butyl lithium (15% in hexane, 0.1 mole) is added to 100 ml. benzene. To this stirred solution dimethylamine is passed until excess had been added. A stream of dry nitrogen, saturated with benzene vapour, is then passed through the solution to remove excess amine. After 15 minutes, 13.9 g. 1-methyl-N-(cyclohexylidene)-ethylamine is added during about 2 minutes producing a pale yellow solution. After a further 15 minutes, 10.3 g. benzonitrile is added during about 2 minutes, producing a dark red/brown solution of the lithium salt of 2-isopropyl-amino-α-phenyl-1-cyclohexene-1-methyleneimine. After one hour, the solution is cooled to 0° and 10.8 g. ethyl chloroformate is added dropwise during about 15 minutes. After one hour, water is added to the reaction mixture and the organic layer washed. The organic layer is extracted with 2NHCl and the acid extracts then basified. Extraction of this basic mixture with methylene chloride, followed by drying and evaporation of the extracts, gives an oil which crystallizes from acetone as 1-isopropyl-4-phenyl-5,6,7,8-tetrahydro-2(1H)-quinazolinone, m.p. 176–177.

EXAMPLE 2

1-Isopropyl-4-Phenyl-5,6,7,8-Tetrahydro-2(1H)-Quinazolinone

To 5.05 g. diisopropylamine in 50 ml. dry benzene is added butyl lithium (31.5 ml. of a 1.6N solution in hexane). After 15 minutes, 7.65 g. of 1-methyl-N-(cyclohexylidene)-ethylamine prepared as in Example 1 is added during about 2 minutes. 5.5 g. benzonitrile is added after 10 minutes to give a deep red solution, and after a further 10 minutes about 5 ml. of water are added, causing the color to change to pale yellow. After 30 minutes, 5 g. of phosgene in a 12.5% solution in benzene is added dropwise to this mixture at 0°. After 1 hour, the reaction was worked up as in Example 1 to give the same product.

EXAMPLE 3

6-Methyl-1-Isopropyl-4-Phenyl-5,6,7,8-Tetrahydro-2-(1H)-Quinazolinone.

Step A: 1-Methyl-N-(4-methyl cyclohexlidene)-ethylamine

To a mixture of 600 g. 4-methyl cyclohexanone and 1 l. isopropylamine are added 500 g. Linde Type 3A molecular sieves. The mixture is allowed to stand overnight at room temperature, after which the sieves are removed by filtration and the excess of isopropylamine is removed in vacuo at room temperature. The residual oil is 1-methyl-N-(4-methyl cyclohexylidene)-ethylamine.

Step B: 0.3 moles n-butyl-lithium (in a 1.6N solution of hexane) is added to a solution of 30.3 g. diisopropylamine in 300 ml. benzene. After 15 minutes, there is added, during about 2 minutes, 45 g. of 1-methyl-N-(4-methyl cyclohexylidene)-ethylamine and after a further 15 minutes 30.9 g. benzonitrile are added during about 2 minutes, producing a solution of the lithium salt of 5-methyl-2-isopropylamino-α-phenyl-1-cyclohexene-1-methylenimine. After 30 minutes, 500 ml. water is added to the reaction mixture and the organic layer washed several times with water. The organic layer is then dried and evaporated to yield a yellow oil.

Step C: 6-Methyl-1-isopropyl-4-phenyl-5,6,7,8-tetrahyro-2(1H)-quinazolinone The oily product of Step B is dissolved in 400 ml. toluene together with 60.6 g. triethylamine and the solution added dropwise during about 30 minutes to a stirred solution of 60 g. phosgene in 1 l. toluene at 0°. The mixture is stirred for a further 1 hour at room temperature and then water is added. Work-up as in Example 1 and recrystallization from acetone/ether yields crystals of 6-methyl-1-isopropyl-4-phenyl-5,6,7,8-tetrahydro-2(1H)-quinazolinone, m.p. 175°-177°.

EXAMPLE 4

7-Methyl-1-Isopropyl-4-Phenyl-5,6,7,8-tetrahydro-2(1H)-Quinazolinone.

Step A: Preparation of 1-methyl-N-(3-methylcyclohexylidene)-ethylamine

To a mixture of 112 g. 3-methyl cyclohexanone and 120 g. isopropylamine are added 100 g. Linde Type 3A molecular sieves. The mixture is allowed to stand overnight at room temperature, after which the sieves are removed by filtration and the excess of isopropylamine is removed in vacuo at room temperature. The oil residue is 1-methyl-N-(3-methyl cyclohexylidene)-ethylamine, b.p. 36 to 0.5 mm.

Step B: 4-Methyl-2-isopropylamino-α-phenyl-1-cyclohexene-1-methylenimine 2.0 moles of n-butyl lithium (in a 1.6N solution in hexane) are added to a solution of 202 g. of diisopropylamine in 2 l. benzene. After 15 minutes 306 g. of 1-methyl-N-(3-methyl cyclohexylidene)-ethylamine are added while stirring. After a further 30 minutes, 206 g. benzonitrile are added to the mixture stirred for 45 minutes, producing a solution of the lithium salt of 4-methyl-2-isopropylamino-α-phenyl-cyclohexene-1-methylenimine. The reaction is then swamped with water and the organic layers washed 3 times with water. The organic layer is then dried and evaporated. The yellow oily residue is then distilled and 4-methyl-2-isopropylamino-α-phenyl-1-cyclohexene-1-methylenimine collected at 155°/0.7 mm.

Step C: 7-Methyl-1-isopropyl-4-phenyl-5,6,7,8-tetrahydro-2(1H)-quinazolinone A solution of 239 g. 4-methyl-2-isopropylamino-α-phenyl-1-cyclohexene-1-methylenimine and 172 g. triethylamine in 1 l. toluene is added dropwise during 30 minutes to a solution of 170 g. phosgene in 2 l. toluene at 0°. After 1 hour stirring water is added and the resulting mixture worked up as in Example 1 to give 7-methyl-1-isopropyl-4-phenyl-5,6,7,8-tetrahydro-2(1H)-quinazolinone, m.p. 150°-153°.

The following examples illustrate various methods of dehydrogenating the tetrahydro compounds produced by the process of this invention.

EXAMPLE A

To 14 g. of 7-methyl-1-isopropyl-4-phenyl-5,6,7,8-tetrahydro 2(1H)-quinazolinone in 280 ml. xylene is added 0.35 g. palladium on charcoal catalyst (10%) and the mixture refluxed for 24 hours. The catalyst is then removed by filtration and the filtrate evaporated to leave a crystalline residue which crystallizes from ethyl acetate to yield 7-methyl-1-isopropyl-4-phenyl-4,5-dihydro 2(1H)-quinazolinone.

EXAMPLE B

To 14 g. of 7-methyl-1-isopropyl-4-phenyl-5,6,7,8-tetrahydro-2(1H)-quinazolinone in 280 ml. xylene is added 0.70 g. palladium on charcoal catalyst (10%) and 3.5 ml. nitrobenzene and the mixture refluxed for 24 hours. The catalyst is then removed by filtration and the filtrate evaporated. The residue crystallized from ethyl acetate is a mixture of 7-methyl-1-isopropyl-4-phenyl-2(1H)-quinazolinone and 7-methyl-1-isopropyl-4,5-dihydro-2(1H)-quinazolinone in a ratio of approximately 2:1.

EXAMPLE C

To 50 ml. of xylene are added 1.35 g. of 7-methyl-1-isopropyl-4-phenyl-5,6,7,8-tetrahydro-2(1H)-quinazolinone and 0.32 g. sulfur. The mixture is boiled overnight (about 16 hours). The resulting solution is evaporated under pressure and the catalyst crystalline residue is recrystallized from ether/petroleum ether to give 7-methyl-1-isopropyl-4-phenyl-2(1H)-quinazolinone.

I claim:
1. A compound of the formula:

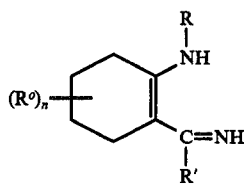

wherein
R° is alkyl of 1 to 3 carbon atoms,
n is 0, 1 or 2,
R is alkyl of 1 to 5 carbon atoms, and
R' is a group of the formula

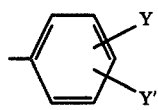

in which Y and Y' are independently hydrogen, alkyl of 1 to 2 carbon atoms, alkoxy of 1 or 2 carbon atoms, fluoro or chloro or one of Y and Y' is trifluoromethyl while the other is hydrogen, or a group of the formula

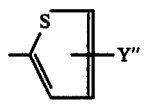

in which Y" is hydrogen, fluoro, chloro, or alkyl of 1 to 3 carbon atoms.

2. The compound of claim 1 which is 4-methyl-2-isopropylamino-α-phenyl-1-cyclohexene-1-methylenimine.

3. A solution of a salt of the formula:

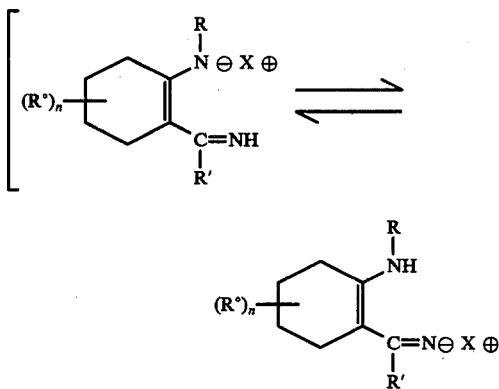

wherein
R° is alkyl of 1 to 3 carbon atoms,
n is 0, 1 or 2,
R is alkyl of 1 to 5 carbon atoms,
R' is a group of the formula

in which Y and Y' are independently hydrogen, alkyl of 1 to 2 carbon atoms, alkoxy of 1 or 2 carbon atoms, fluoro or chloro or one of Y and Y' is trifluoromethyl while the other is hydrogen, or a group of the formula

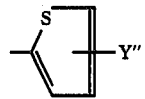

in which Y" is hydrogen, fluoro, chloro or alkyl of 1 to 3 carbon atoms, and is magnesium or an alkali metal.

4. A solution of claim 3 in which the salt is the lithium salt of 2-isopropylamino-α-phenyl-1-cyclohexene-1-methylenimine.

5. A salt of claim 3 in which X is lithium or magnesium.

6. A salt of claim 3 in which X is lithium.

7. A process for producing a compound of claim 1 which comprises reacting a cyclohexylidine of the formula:

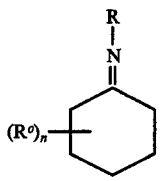

in which R, R° and n are defined in claim 1 with:
1. a metal-containing base selected from the group consisting of methyl magnesium iodide and an alkali metal salt of a secondary amine; and 2 a compound of the formula:

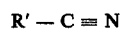

in which R' is as defined in claim 1, in an inert solvent to form a solution of the Salt A:

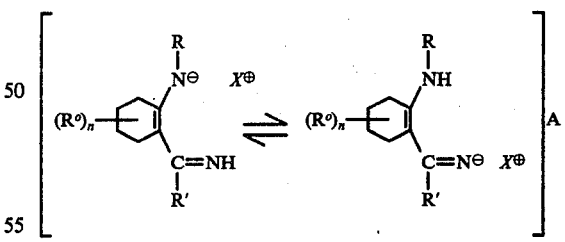

in which R, R°, R' and n are as defined in claim 1, and X is magnesium or an alkali metal corresponding to the metal in the base, and quenching said solution with water.

8. The process of claim 7 in which X is magnesium or lithium.

9. The process of claim 7 in which the base is the lithium salt of dimethylamine, diethylamine or diisopropylamine and X is lithium.

10. The process of claim 9 in which the base is lithium diisopropylamine and R° is an alkyl group in the meta position of the cyclohexylidene.

* * * * *

UNITED STATES PATENT AND TRADEMARK OFFICE
CERTIFICATE OF CORRECTION

PATENT NO. : 4,066,665
DATED : January 3, 1978
INVENTOR(S) : William G. Salmond

It is certified that error appears in the above-identified patent and that said Letters Patent are hereby corrected as shown below:

Column 10, line 8, "alkyl of 1 to 2 carbon atoms," should read --alkyl of 1 or 2 carbon atoms,--.

Column 10, line 18, "to 3 carbon atoms, and is magnesium" should read --to 3 carbon atoms, and X is magnesium--.

Signed and Sealed this

Tenth Day of July 1979

[SEAL]

Attest:

LUTRELLE F. PARKER
*Attesting Officer*     *Acting Commissioner of Patents and Trademarks*